US009445840B2

(12) United States Patent
Han et al.

(10) Patent No.: US 9,445,840 B2
(45) Date of Patent: Sep. 20, 2016

(54) INTEGRATED MICROFLUIDIC DEVICE FOR SINGLE OOCYTE TRAPPING

(75) Inventors: Chao Han, Beijing (CN); Guoliang Huang, Beijing (CN); Jing Cheng, Beijing (CN)

(73) Assignees: Tsinghua University, Beijing (CN); CapitalBio Corporation, Beijing (CN)

( * ) Notice: Subject to any disclaimer, the term of this patent is extended or adjusted under 35 U.S.C. 154(b) by 591 days.

(21) Appl. No.: 13/805,322

(22) PCT Filed: Jun. 17, 2011

(86) PCT No.: PCT/CN2011/001013
§ 371 (c)(1),
(2), (4) Date: Mar. 4, 2013

(87) PCT Pub. No.: WO2011/160430
PCT Pub. Date: Dec. 29, 2011

(65) Prior Publication Data
US 2013/0204076 A1 Aug. 8, 2013

(30) Foreign Application Priority Data
Jun. 25, 2010 (CN) .......................... 2010 1 0218520

(51) Int. Cl.
*A61B 17/43* (2006.01)
*A61B 17/435* (2006.01)
(Continued)

(52) U.S. Cl.
CPC ............. *A61B 17/43* (2013.01); *A61B 17/435* (2013.01); *B01L 3/502761* (2013.01);
(Continued)

(58) Field of Classification Search
CPC ................ A61B 17/435; A61B 17/43; B01L 3/502761; B01L 2200/0652; B01L 2300/0851; B01L 2400/086; B01L 2200/0689
See application file for complete search history.

(56) References Cited

U.S. PATENT DOCUMENTS 6,193,647 B1 * 2/2001 Beebe et al. .................... 600/33
6,695,765 B1 2/2004 Beebe et al.
(Continued)

FOREIGN PATENT DOCUMENTS

CN 1441652 9/2003
CN 1909847 2/2007
(Continued)

OTHER PUBLICATIONS

International Preliminary Report on Patentability and Written Opinion for PCT/CN2011/001013, issued Dec. 28, 2012, 5 pages.
(Continued)

*Primary Examiner* — Christine H Matthews
*Assistant Examiner* — Joshua D Lannu
(74) *Attorney, Agent, or Firm* — Morrison & Foerster LLP; Peng Chen; Bu Yin

(57) ABSTRACT

An integrated microfluidic device and its usage are provided. The microfluidic device comprises an upper layer (1) and a lower layer (2), wherein the lower layer (2) is bound to the upper layer (1). The upper layer (1) comprises a micro-channel (3) and the lower layer (2) comprises a micro-well (7) array. The micro-channel (3) is in fluidic connection with the micro-well (7) array, and the height of the micro-channel (3) is greater than the diameter of the oocyte (4) flowing through the micro-channel (3). The integrated microfluidic device has many advantages including low cost, high integration, and convenient operation, and has application prospects in reproductive medicine and the research of fertilization and embryo early development.

41 Claims, 3 Drawing Sheets

(51) Int. Cl.
  *B01L 3/00* (2006.01)
  *C12M 3/00* (2006.01)
  *C12M 3/06* (2006.01)
  *C12M 1/00* (2006.01)

(52) U.S. Cl.
  CPC ............... *B01L 2200/0652* (2013.01); *B01L 2200/0689* (2013.01); *B01L 2300/0851* (2013.01); *B01L 2400/086* (2013.01); *C12M 21/06* (2013.01); *C12M 23/16* (2013.01); *C12M 47/04* (2013.01)

(56) References Cited

U.S. PATENT DOCUMENTS

2002/0182631 A1* 12/2002 Schurmann-Mader et al. .. 435/6
2003/0180191 A1* 9/2003 Suzuki et al. ................ 422/102
2007/0264705 A1* 11/2007 Dodgson ..................... 435/283.1
2007/0266801 A1* 11/2007 Khademhosseini . B01J 19/0046
  73/863.91
2009/0298116 A1* 12/2009 Fang et al. ..................... 435/29

FOREIGN PATENT DOCUMENTS

| | | |
|---|---|---|
| CN | 101446583 | 6/2009 |
| WO | WO-2004/108011 | 12/2004 |
| WO | WO-2005/023124 | 3/2005 |
| WO | WO-2010/008977 | 1/2010 |

OTHER PUBLICATIONS

International Search Report for PCT/CN2011/001013, mailed Oct. 13, 2011, 7 pages.

* cited by examiner

INTEGRATED MICROFLUIDIC DEVICE FOR SINGLE OOCYTE TRAPPING

CROSS-REFERENCE TO RELATED APPLICATIONS

This application is the national phase of PCT application PCT/CN2011/001013 having an international filing date of Jun. 17, 2011, which claims priority to Chinese Patent Application No. 201010218520.1, filed on Jun. 25, 2010. The contents of the above-listed applications are incorporated herein by this reference in their entireties.

TECHNICAL FIELD

The present invention relates to an integrated microfluidic device and its uses for single oocyte trapping. The present invention further relates to methods of oocyte trapping, in vitro fertilization (IVF), liquid manipulation, and embryo culture and retrieval using the integrated microfluidic device.

BACKGROUND ART

In vitro fertilization, a medical technology by which oocyte cells are fertilized by sperms in vitro, is currently a major treatment for infertility in clinics. The standard protocols for clinical IVF practice include gametes collection, fertilization, liquid manipulation and embryo culture, with culture medium held in oil-covered drops in Petri dishes, and manipulation performed manually by pipetting. For these protocols, frequent pipetting of gametes is required, which is labor-intensive and time-consuming. Furthermore, fertilization and embryo culture require different media, therefore the zygotes have to be washed several times and transported to different drops for further development. Although some culture media have been developed to support both fertilization and embryo development (Complete HTF Medium with SSSTM, Irvine Scientific, Santa Ana, Calif.), the oocyte-washing step to remove sperm debris is still mandatory. Another issue involves the ability to track the fertilization and development of an individual oocyte, since oocytes are typically fertilized, washed, transferred and cultured in groups under the standard protocols.

Microfluidic chip has great potential for IVF. Compared with conventional IVF technology, micro-channels and micro-structures can be flexibly designed for oocytes manipulation and positioning, providing the fertilization process better controllability. Because of the advantage of integration, microfluidic chip may also integrate the process of fertilization and embryo culture on a single chip. U.S. Pat. No. 6,193,647 B1 describing oocyte trapping and IVF with such a microfluidic chip includes a constricted channel to position the oocyte, which may not only harm the oocyte by large fluid shear stress, but also is not suitable for the simultaneous positioning of multiple oocytes. PCT Publication No. WO 2005/023124 A2 describes a series of micro-wells under a narrow micro-channel, so that the oocytes could be transferred in the channel and trapped in the micro-wells. However, the device described in WO 2005/023124 A2 has several disadvantages: 1) the micro-channel in the device is too narrow, so that fast sperm sample loading or liquid manipulation processes are not available; 2) the depth of wells in the device is not optimized, considering its influence on the positioning of oocytes; 3) the device didn't overcome the problem of dead sperm and cell debris removal; and 4) the process of oocyte or embryo retrieval is based on fluid flushing or turning the device upside down, which adds complexity to the operation. In conclusion, there exists a need for a microfluidic device that integrates high-throughput single oocyte trapping, fertilization, fast liquid manipulation, embryo culture and convenient embryo retrieval.

SUMMARY OF THE INVENTION

The present invention relates to a microfluidic device and its method of use for oocyte trapping, in vitro fertilization, fast liquid manipulation, and embryo culture and retrieval.

Therefore, in one aspect, provided herein is an integrated microfluidic device for single oocyte trapping, said microfluidic device comprises an upper layer and a lower layer, wherein said lower layer is bound to said upper layer, said upper layer comprises a micro-channel and said lower layer comprises a micro-well array, said micro-channel is in fluidic connection with said micro-well array, and the height of said micro-channel is greater than the diameter of said oocyte.

In some embodiments, the micro-wells have the same or different depths. In some embodiments, the depth of the micro-well array may be greater than the diameter of the oocyte. In some embodiments, the depth of the micro-well array may be at least twice the diameter of the oocyte. In some embodiments, the micro-wells may have the same or different widths. In some embodiments, the width of the micro-wells may be greater than the diameter of the oocyte. In some embodiments, the width of the micro-wells may be at least 1.5 times the diameter of the oocyte. In some embodiments, the micro-wells may be distributed in parallel and/or perpendicular to the direction of the fluidic flow in the micro-channel. In some embodiments, the micro-well array may cover the whole width of the micro-channel. In some embodiments, the distance between adjacent micro-well rows may be smaller than half of the width of the micro-well. In some embodiments, the distance between adjacent micro-well rows may be less than ¼, ⅓, or ½ of the width of the micro-well. In some embodiments, the micro-wells may have a shape of square, circle or any other shape. In some embodiments, the micro-wells may have the same or different shapes. In some embodiments, the upper layer and/or lower layer may be made of a transparent material. In some embodiments, the upper layer and/or lower layer may be made of polydimethylsiloxane (PDMS). In some embodiments, a layer of reflective material may be attached beneath the micro-well array. In some embodiments, the upper layer may be reversibly bound to the lower layer. In some embodiments, the upper layer may further comprise an inlet and/or an outlet to the micro-channel. In some embodiments, the device may further comprise an oocyte or a plurality of separated trapped oocytes.

Also provided herein is a use of the integrated microfluidic device disclosed above for trapping oocytes. In some embodiments, the oocyte may be a mammalian oocyte In some embodiments, the oocyte may be a murine or human oocyte. In some embodiments, the integrated microfluidic device may be used for high-throughput oocyte trapping. In some embodiments, the integrated microfluidic device may comprise at least 5, 10, 20, 30, 40, 50, 100 or more micro-wells.

Further provided herein is a system for single oocyte trapping comprising an integrated microfluidic device, said microfluidic device comprises an upper layer and a lower layer, wherein said lower layer is bound to said upper layer, said upper layer comprises a micro-channel and said lower layer comprises a micro-well array, said micro-channel is in fluidic connection with said micro-well array, and the height of said micro-channel is greater than the diameter of said oocyte.

In some embodiments, the system for single oocyte trapping may further comprise a delivering means to introduce the oocyte to the micro-channel. In some embodiments, the system for single oocyte trapping may further comprise an injecting means to introduce a liquid into the micro-channel. In some embodiments, the system for single oocyte trapping may further comprise a retrieving means to remove the oocyte from the micro-wells. In some embodiments, the system for single oocyte trapping may further comprise an interferometer.

Additionally, provided herein is a method for single oocyte trapping using the integrated microfluidic device disclosed above comprising: a) transporting oocytes by a liquid in the micro-channel, wherein said oocytes enter the micro-well array. In some embodiments, the method may further comprise: b) adding sperms to the micro-channel, wherein in vitro fertilization occurs in the micro-well array. In some embodiments, the method may further comprise: c) adding a new liquid to the micro-channel, wherein dead sperms and cell debris in said micro-channel are removed to facilitate further development of fertilized eggs. In some embodiments, the method may further comprise: d) retrieving fertilized eggs or embryos from the micro-well array.

In some embodiments, the microfluidic device may be placed in an incubator, e.g., a $CO_2$ incubator. In some embodiments, the liquid in the micro-channel may be held still to allow sperms to swim to the micro-well array and enter the micro-wells. In some embodiments, the liquid in the micro-channel may be used to transport the sperms to the micro-well array. In some embodiments, the new liquid may be added by pipetting, and wherein the fluid in the micro-channel may be driven by the height difference between the ends of the micro-channel. In some embodiments, one end of the micro-channel may be connected with a syringe pump or similar device, and wherein the new liquid may be injected by positive or negative pressure. In some embodiments, the liquid stays still, or flows constantly or intermittently, during the embryo culture process. In some embodiments, after the sperms reach the oocytes, air may be introduced into the micro-channel to replace the liquid, so that micro-droplets are formed in the micro-wells, and an oil phase liquid may be added into the micro-channel to seal the micro-droplets. In some embodiments, fertilization of the oocytes by the sperms may be realized in the sealed micro-droplet. In some embodiments, after fertilization of the oocytes or development of the fertilized eggs or embryos, air may be introduced into the micro-channel to replace the liquid, so that micro-droplets are formed in the micro-wells, and an oil phase liquid may be added into the micro-channel to seal the micro-droplets. In some embodiments, development of the fertilized eggs or embryos may be realized in the sealed micro-droplet. In some embodiments, the upper layer may be removed from the lower layer to expose the micro-well array for retrieving fertilized eggs or embryos from the micro-well array.

Figure 7:
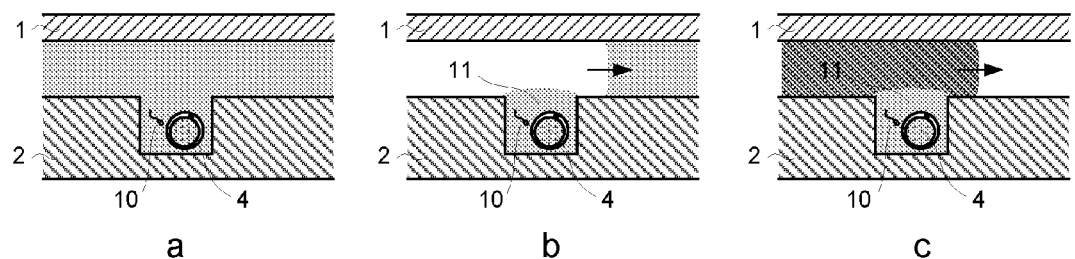

Panels a, b, and c of FIG. 7 are schematic diagrams showing embodiments of IVF using the microfluidic device.

DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

As used herein, the term "microfluidic device" generally refers to a device through which materials, particularly fluid borne materials, such as liquids, can be transported, in some embodiments on a micro-scale, and in some embodiments on a nanoscale. Thus, the microfluidic devices described by the presently disclosed subject matter can comprise microscale features, nanoscale features, and combinations thereof.

Accordingly, an exemplary microfluidic device typically comprises structural or functional features dimensioned on the order of a millimeter-scale or less, which are capable of manipulating a fluid at a flow rate on the order of a µL/min or less. Typically, such features include, but are not limited to channels, fluid reservoirs, reaction chambers, mixing chambers, and separation regions. In some examples, the channels include at least one cross-sectional dimension that is in a range of from about 0.1 µm to about 500 µm. The use of dimensions on this order allows the incorporation of a greater number of channels in a smaller area, and utilizes smaller volumes of fluids.

A microfluidic device can exist alone or can be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current, and the like.

As used herein, the terms "channel," "micro-channel," and "microfluidic channel" are used interchangeably and can mean a recess or cavity formed in a material by imparting a pattern from a patterned substrate into a material or by any suitable material removing technique, or can mean a recess or cavity in combination with any suitable fluid-conducting structure mounted in the recess or cavity, such as a tube, capillary, or the like.

As used herein, the terms "flow channel" and "control channel" are used interchangeably and can mean a channel in a microfluidic device in which a material, such as a fluid, e.g., a gas or a liquid, can flow through. More particularly, the term "flow channel" refers to a channel in which a material of interest, e.g., a solvent or a chemical reagent, can flow through. Further, the term "control channel" refers to a flow channel in which a material, such as a fluid, e.g., a gas or a liquid, can flow through in such a way to actuate a valve or pump.

As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include channels or wells fabricated on the surfaces.

As used herein, the term "oocyte" refers to a female gamete cell and includes primary oocytes, secondary oocytes and mature, unfertilized ovum. An oocyte is a large cell having a large nucleus (i.e., the germinal vesicle) surrounded by ooplasm. The ooplasm contains non-nuclear cytoplasmic contents including mRNA, ribosomes, mitochondria, yolk proteins, etc. The membrane of the oocyte is referred to herein as the "plasma membrane."

As used herein, the term "egg," when used in reference to a mammalian egg, means an oocyte surrounded by a zona pellucida and a mass of cumulus cells (follicle cells) with their associated proteoglycan. The term "egg" is used in reference to eggs recovered from antral follicles in an ovary (these eggs comprise pre-maturation oocytes) as well as to eggs which have been released from an antral follicle (a ruptured follicle).

The term "pre-maturation oocyte," as used herein refers to a female gamete cell following the oogonia stage (i.e., mitotic proliferation has occurred) that is isolated from an ovary (e.g., by aspiration) but which has not been exposed to maturation medium in vitro. Those of skill in the art know that the process of aspiration causes oocytes to begin the maturation process but that completion of the maturation process (i.e., formation of a secondary oocyte which has extruded the first polar body) in vitro requires the exposure of the aspirated oocytes to maturation medium. Pre-maturation oocytes will generally be arrested at the first anaphase of meiosis.

The term "pre-fertilization oocyte" as used herein, refers to a female gamete cell such as a pre-maturation oocyte following exposure to maturation medium in vitro but prior to exposure to sperm (i.e., matured but not fertilized). The pre-fertilization oocyte has completed the first meiotic division, has released the first polar body and lacks a nuclear membrane (the nuclear membrane will not reform until fertilization occurs; after fertilization, the second meiotic division occurs along with the extrusion of the second polar body and the formation of the male and female pronuclei). Pre-fertilization oocytes may also be referred to as matured oocytes at metaphase 11 of the second melosis.

The terms "unfertilized egg" or "unfertilized oocyte" as used herein, refers to any female gamete cell which has not been fertilized and these terms encompass both pre-maturation and pre-fertilization oocytes.

The term "zygote" as used herein, refers to a fertilized oocyte that has not yet undergone the first cleavage step in the development of an embryo (i.e., it is at the single-cell stage). high-throughput single oocyte trapping As used herein, "high-throughput single oocyte trapping" refers to simultaneous trapping of multiple oocytes, wherein at least 5, 10, 20, 30, 40, 50, 100 or more oocytes are trapped in individual spaces, e.g., micro-wells, in a fashion involving minimal manipulation.

As used herein, "medium" or "culture medium" refers to a fluidic carrier, e.g., liquid or gas, wherein cells are dissolved, suspended or contained.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

B. Integrated Microfluidic Device

One objective of the present invention is to provide an integrated microfluidic device and uses thereof for oocyte trapping, in vitro fertilization, fast liquid manipulation, and embryo culture and retrieval.

To achieve the above mentioned objective, in one aspect, the present invention provides an integrated microfluidic device for single oocyte trapping, said microfluidic device comprises an upper layer and a lower layer, wherein said lower layer is bound to said upper layer, said upper layer comprises a micro-channel and said lower layer comprises a micro-well array, said micro-channel is in fluidic connection with said micro-well array, and the height of said micro-channel is greater than the diameter of said oocyte.

The microfluidic devices of the present invention may comprise a central body structure in which various microfluidic elements are disposed. The body structure includes an exterior portion or surface, as well as an interior portion which defines the various microscale channels and/or chambers of the overall microfluidic device. For example, the body structure of the microfluidic devices of the present invention typically employs a solid or semi-solid substrate that may be planar in structure, i.e., substantially flat or having at least one flat surface. Suitable substrates may be fabricated from any one of a variety of materials, or combinations of materials. Often, the planar substrates are manufactured using solid substrates common in the fields of microfabrication, e.g., silica-based substrates, such as glass, quartz, silicon or polysilicon, as well as other known substrates, i.e., gallium arsenide. In the case of these substrates, common microfabrication techniques, such as photolithographic techniques, wet chemical etching, micromachining, i.e., drilling, milling and the like, may be readily applied in the fabrication of microfluidic devices and substrates. Alternatively, polymeric substrate materials may be used to fabricate the devices of the present invention, including, e.g., polydimethylsiloxanes (PDMS), polymethylmethacrylate (PMMA), polyurethane, polyvinylchloride (PVC), polystyrene, polysulfone, polycarbonate and the like. In the case of such polymeric materials, injection molding or embossing methods may be used to form the substrates having the channel and reservoir geometries as described herein. In such cases, original molds may be fabricated using any of the above described materials and methods.

The channels and chambers of the device are typically fabricated into one surface of a planar substrate, as grooves, wells or depressions in that surface. A second planar substrate, typically prepared from the same or similar material, is overlaid and bound to the first, thereby defining and sealing the channels and/or chambers of the device. Together, the upper surface of the first substrate, and the lower mated surface of the upper substrate, define the interior portion of the device, i.e., defining the channels and chambers of the device. In some embodiments, the upper layer may be reversibly bound to the lower layer.

In the exemplary devices described herein, at least one main channel, also termed an analysis channel, is disposed in the surface of the substrate through which samples are transported and subjected to a particular analysis. Typically, a number of samples are serially transported from their respective sources, and injected into the main channel by placing the sample in a transverse channel that intersects the main channel. This channel is also termed a "sample loading channel." The sample sources are preferably integrated into the device, e.g., as a plurality of wells disposed within the device and in fluid communication with the sample loading channel, e.g., by an intermediate sample channel.

The lower layer of the device described herein may comprise a number of micro-wells that are in fluidic connection with the micro-channel in the upper layer, which may form an array. In some embodiments, the micro-wells are distributed in parallel and/or perpendicular to the direction of the fluidic flow in the micro-channel. In some embodiments, the micro-well array covers the whole width of the micro-channel. In some embodiments, the distance between adjacent micro-well rows may be smaller than half of the width of the micro-well. In some embodiments, the distance between adjacent micro-well rows may be less than $\frac{1}{4}$, $\frac{1}{3}$, or $\frac{1}{2}$ of the width of the micro-well. In some embodiments, the micro-wells have the same or different depths. In some embodiments, the depth of the micro-well array may be greater than the diameter of the oocyte. In some embodiments, the depth of the micro-well array may be at least twice the diameter of the oocyte. In some embodiments, the micro-wells have the same or different widths. In some embodiments, the width of the micro-wells may be greater than the diameter of the oocyte. In some embodiments, the width of the micro-wells may be at least 1.5 times the diameter of the oocyte. In some embodiments, the micro-wells have a shape of square, circle or any other shape. In some embodiments, the micro-wells have the same or different shapes. In some embodiments, the upper layer and/or lower layer may be made of a transparent material. In some embodiments, a layer of reflective material may be attached beneath the micro-well array. In some embodiments, the device may further comprise an oocyte or a plurality of separated trapped oocytes.

Further provided herein is a system for single oocyte trapping comprising an integrated microfluidic device, said microfluidic device comprises an upper layer and a lower layer, wherein said lower layer is bound to said upper layer, said upper layer comprises a micro-channel and said lower layer comprises a micro-well array, said micro-channel is in fluidic connection with said micro-well array, and the height of said micro-channel is greater than the diameter of said oocyte.

The systems of the invention may also include sample sources that are external to the body of the device per se, but still in fluid communication with the sample loading channel. In some embodiments, the system for single oocyte trapping may further comprise an inlet and/or an outlet to the micro-channel. In some embodiments, the system for single oocyte trapping may further comprise a delivering means to introduce the oocyte to the micro-channel. In some embodiments, the system for single oocyte trapping may further comprise an injecting means to introduce a liquid into the micro-channel. Any liquid manipulating equipments, such as pipettes, pumps, etc., may be used as an injecting means to introduce a liquid to the micro-channel. In some embodiments, the system for single oocyte trapping may further comprise a retrieving means to remove the oocyte from the micro-wells. Any suitable equipments, such as pipettes, microfluidic pumps, etc., may be used as a retrieving means to remove the oocyte, fertilized egg, or embryo from the micro-wells. In some embodiments, the system for single oocyte trapping may further comprise an interferometer. Other optical detection devices known in the art may also be included in the system for single oocyte trapping for monitoring, e.g., real-time monitoring, the fertilized egg or embryos in the micro-well array.

C. Methods of Oocyte Trapping, Fertilization and Retrieval

Another object of the present invention is to provide methods of single oocyte trapping, in vitro fertilization, fast liquid manipulation, and embryo culture and retrieval, using the integrated microfluidic device disclosed above.

Therefore, in another aspect, provided herein is a use of the integrated microfluidic device disclosed above for trapping oocytes. In some embodiments, the oocyte may be a mammalian oocyte In some embodiments, the oocyte may be a murine or human oocyte. In some embodiments, the integrated microfluidic device may be used for high-throughput oocyte trapping. In some embodiments, the integrated microfluidic device may comprise at least 5, 10, 20, 30, 40, 50, 100 or more micro-wells.

Additionally, provided herein is a method for single oocyte trapping using the integrated microfluidic device disclosed above comprising: a) transporting oocytes by a liquid in the micro-channel, wherein said oocytes enter the micro-well array. In some embodiments, the method may further comprise: b) adding sperms to the micro-channel, wherein in vitro fertilization occurs in the micro-well array. In some embodiments, the method may further comprise: c) adding a new liquid to the micro-channel, wherein dead sperms and cell debris in said micro-channel are removed to facilitate further development of fertilized eggs. In some embodiments, the method may further comprise: d) retrieving fertilized eggs or embryos from the micro-well array.

In some embodiments, the microfluidic device may be placed in a $CO_2$ incubator. In some embodiments, the liquid in the micro-channel may be held still, and the sperms swim to the micro-well array and enter the micro-wells. In some embodiments, the liquid in the micro-channel may be used to transport the sperms to the micro-well array. In some embodiments, the new liquid may be added by pipetting, and wherein the fluid in the micro-channel may be driven by the height difference between the ends of the micro-channel. In some embodiments, one end of the micro-channel may be connected with a syringe pump or similar device, and wherein the new liquid may be injected by positive or negative pressure. In some embodiments, the liquid stays still, or flows constantly or intermittently, during the embryo culture process. In some embodiments, after the sperms reach the oocytes, air may be introduced into the micro-channel to replace the liquid, so that micro-droplets are formed in the micro-wells, and an oil phase liquid may be added into the micro-channel to seal the micro-droplets. In some embodiments, fertilization of the oocytes by the sperms may be realized in the sealed micro-droplet. In some embodiments, after fertilization of the oocytes or development of the fertilized eggs or embryos, air may be introduced into the micro-channel to replace the liquid, so that micro-droplets are formed in the micro-wells, and an oil phase liquid may be added into the micro-channel to seal the micro-droplets. In some embodiments, development of the fertilized eggs or embryos may be realized in the sealed micro-droplet. In some embodiments, the upper layer may be removed from the lower layer to expose the micro-well array for retrieving fertilized eggs or embryos from the micro-well array.

The present exemplary embodiments have the following advantages:

1) In some embodiments, more than one micro-well may be included to trap the oocytes. An oocyte may be transported by culture medium along the micro-channel to the top of a micro-well and enter the micro-well by its own gravity. Because the position of single oocyte is determined and remained after trapping, the present invention facilitates the tracking of each oocyte's development and the evaluation of the embryo's development.

2) The size of the micro-wells in the present invention may be designed according to the diameter of oocytes of different species, which not only prevents the oocytes to be flushed out by flow of the medium with the sperms during fertilization, but also facilitates the removal of dead sperms and cell debris.

3) The micro-well structure in the present invention can be easily manufactured with low cost.

4) The upper and lower layer of the chip may be separated, which facilitates the retrieval of selected embryos.

5) Some embodiments may be integrated with many optical detection devices, which enables real-time monitoring of cells from fertilization to further embryo development.

6) In some embodiments, fertilization and/or embryo development may be achieved in a micro-droplet. As the volume of each micro-well is normally in the nanoliter scale, the secretion of the fertilized egg can be well preserved in the micro-droplet, and may promote its own development. Further, because the fertilization process is confined in a small volume, the probability of sperm-egg interaction is greatly increased, thus decreasing the number of sperms needed for effective fertilization.

In summary, the exemplary embodiments have many advantages including low cost, high integration, convenient operation, and will have broad application prospects in reproductive medicine and the research of fertilization and early embryo development.

D. EXAMPLES

The following examples are offered to illustrate but not to limit the invention.

Example 1

Figure 1:
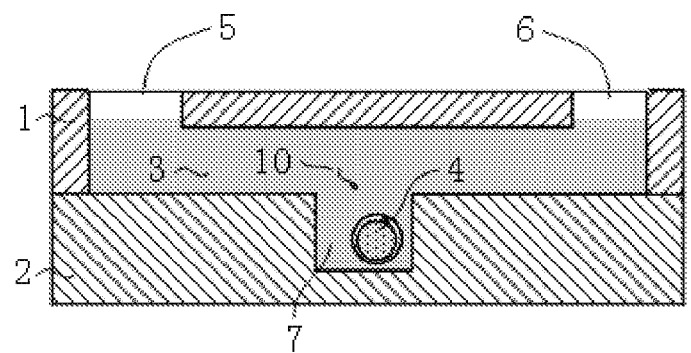
FIG. 1 is a schematic diagram showing one embodiment of the present invention.
Figure 2:
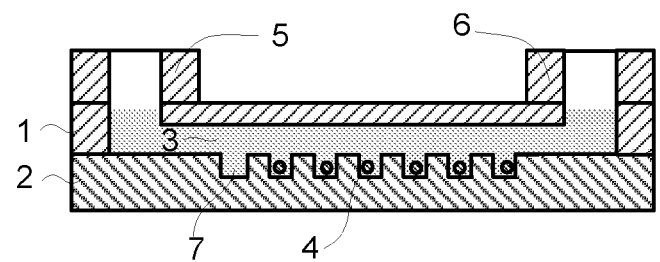
FIG. 2 is a schematic diagram showing another embodiment of the present invention.

FIG. 1 illustrates one embodiment of the present invention of microfluidic chip which comprises an upper micro-channel layer 1 and a lower micro-well array layer 2, and the upper micro-channel layer 1 is closely connected to the lower micro-well layer 2. Micro-channel 3 is designed to be at the bottom of layer 1 and in close contact with layer 2, which has a height greater than the diameter of oocyte transported through it. On the micro-channel layer 1, inlet 5 and outlet 6 are also designed to be connected to the micro-channel 3, which have flexible structures, such as holes or wells (as shown in FIG. 2), or set as interfaces to be connected to other channels. On the micro-well array layer 2, more than one micro-wells 7 are included to trap oocyte 4, which are distributed to form an array both in parallel and vertical to the fluidic direction.

In the above embodiment, oocyte 4 is transferred by culture medium, along the micro-channel 3 in micro-channel layer 1 to the top of one of the micro-wells 7, and drops into the micro-well 7 by its own gravity. Because every oocyte is positioned in a specific micro-well 7, the position is also determined in the micro-well array layer 2. It is easy to track the whole process of fertilization and development of every oocyte, in order to give a comprehensive evaluation of embryo's development. After the oocytes are positioned, sperm 10 is added into the micro-channel 3 through inlet 5. Fertilization process can be realized in either way:

1) The fluid in the micro-channel 3 holds still. Sperm 10 swims from inlet 5 to the micro-well array by its own motility, and enters into micro-well 7, which results in the fertilization of oocyte 4.

2) Sperm 10 is transferred by flowing fluid in micro-channel 3 to the top of and enters micro-well 7, which results in the fertilization of oocyte 4.

Example 2

FIG. 2 illustrates one embodiment of the present invention wherein the micro-well array covers the entire width of micro-channel 3, and along the fluidic direction there is a shift between each row of micro-wells 7 (the shift is smaller than half of the width of the micro-well 7), so as to capture oocytes 4 in different positions in micro-channel 3. Furthermore, the intervals between two micro-wells 7 are smaller than the width of micro-wells 7, which facilitates the entrance by oocyte 4 into the micro-well 7.

In the above embodiment, the shape of micro-well 7 can be square, circle or in any other shapes. The size of micro-well 7 can be designed to fit the size of oocytes of different species, and its width should be larger than the diameter of hatched embryo in order to provide enough space for embryo development.

Example 3

Figure 3:
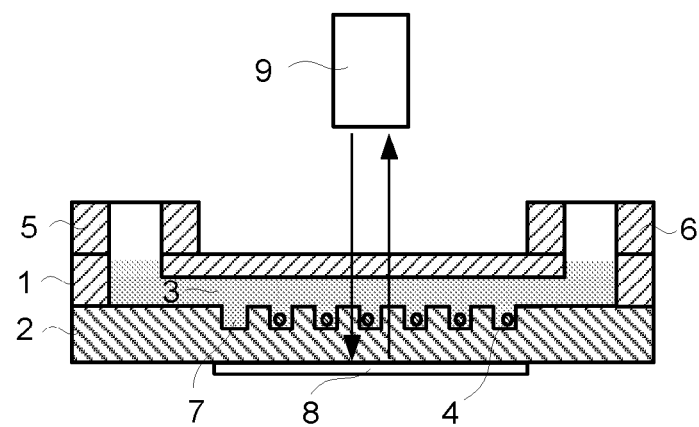
FIG. 3 is a schematic diagram showing the integration of an interferometer into the microfluidic device.

FIG. 3 illustrates one embodiment of the present invention of microfluidic chip which is integrated with an optical detection device such as an interferometer 9. When the materials of micro-channel layer 1 and micro-well array layer 2 are light transparent (e.g., PDMS, etc.), a reflective layer 8 can be placed beneath micro-well array layer 2, and an interferometer 9 can be set on top of micro-channel layer 1. Optical images of oocytes 4 can be obtained by the interferometer 9, providing real-time observation of the fertilization and development process.

Example 4

Figure 4:
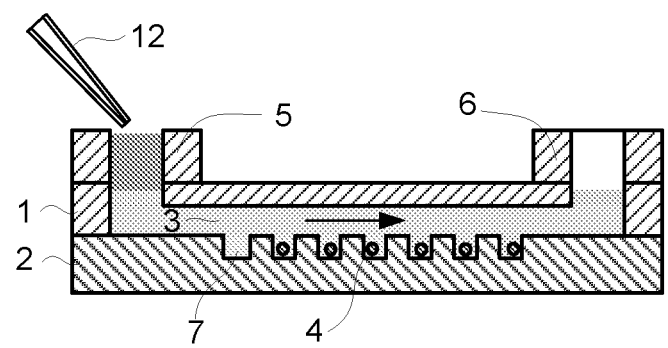
FIG. 4 is a schematic diagram showing one embodiment of the culture medium changing process.
Figure 5:
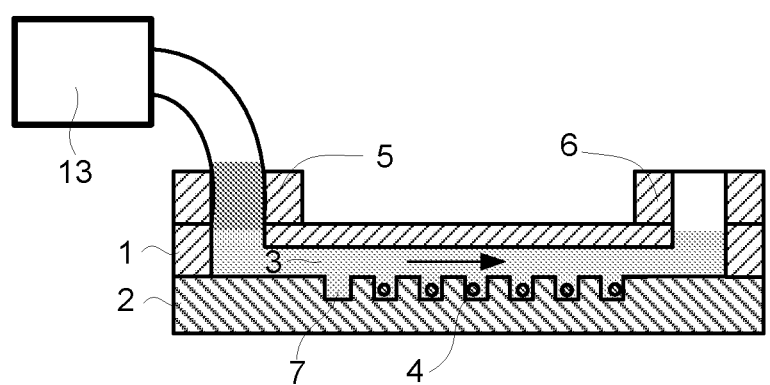
FIG. 5 is a schematic diagram showing another embodiment of the culture medium changing process.

FIGS. 4 and 5 illustrate embodiments of the present invention comprising a rapid medium changing process:

after fertilization occurs, new culture medium is injected from inlet 5 to replace the old culture medium and remove dead sperm 10 and cell debris in micro-channel 3, which facilitates further development of zygotes. Medium may be changed in two ways:

1) As shown in FIG. 4, pipette 12 is used to add new culture medium into inlet 5, and the height difference of liquid levels in inlet 5 and outlet 6 drives the flow in micro-channel 3 (arrow indicates flow direction), which replaces the old medium in micro-channel 3 with new medium and removes dead sperm 10 and cell debris in micro-channel 3. Pipette 12 may also be used to draw the waste from outlet 6. During the medium changing process, micro-wells 7 can effectively prevent the oocytes 4 from being flushed away.

2) As shown in FIG. 5, syringe pump 13 is connected to inlet 5, which introduces the new culture medium into micro-channel 3 by positive pressure. Syringe 13 may also be connected to outlet 6, and drive the new culture medium into micro-channel 3 by negative pressure.

During the fertilization or embryo development process, the microfluidic device may be placed in an ordinary $CO_2$ incubator or other culturing devices to provide an appropriate culturing environment. During embryo development, the culture medium in micro-channel 3 may stand still, or flow constantly or intermittently.

Example 5

Experiments were conducted on murine oocytes, which have a diameter of about 100 μm, to test the relationship between the depth of micro-well 7 and its ability to trap oocyte 4 under high speed of medium flow. Results showed that the trapped oocytes were washed out from micro-wells 7 at 0.128±0.011, 0.500±0.035, 5.10±0.42 and 15.4±0.9 mm/s for the 50, 100, 150 and 200 μm depths, respectively (average and standard deviation calculated from 5 independent experiments). In other words, when the depth of micro-well 7 was larger than 150 μm, the medium changing process could be performed at the flow rate of 5 mm/s, which took several seconds. Thus, when the width of micro-well 7 was twice the diameter of an oocyte, and the depth of micro-well 7 was larger than 1.5 times of the diameter of an oocyte, oocyte positioning was more effective.

Example 6

Figure 6:
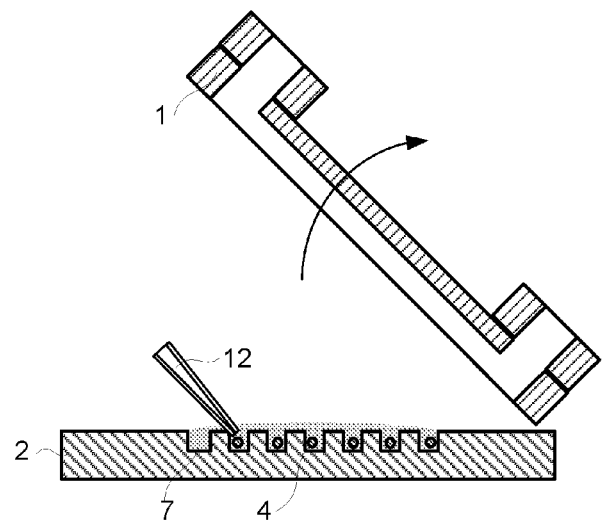
FIG. 6 is a schematic diagram showing one embodiment of the embryo retrieving process.

FIG. 6 illustrates one embodiment of the present invention wherein the embryos in micro-well 7 are retrieved by lifting upper micro-channel layer 1 exposing lower micro-well array layer 2, so that pipettes 12 may be used to retrieve embryos from micro-well 7. The embryo retrieval process can be carried out during embryo stage, or other early stages in development according to different needs.

To achieve dependable and reversible adhesion of micro-channel layer 1 and micro-well array layer 2, and to make the lifting of micro-channel layer 1 possible during the embryo retrieval process, the two layers can be made of PDMS. Because of the good adhesion characteristics of this material, micro-channel layer 1 and micro-well array layer 2 can reversibly stick to each other without leakage. Micro-channel layer 1 may also be made into multiple sections so that the region near inlet 5 and outlet 6 may be irreversibly bound to micro-well array layer 2 to prevent leakage, while the region over the micro-well array may be reversibly bound.

Example 7

FIG. 7 illustrates embodiments of the present invention wherein the fertilization process is conducted with sperm 10 and oocyte 4 sealed in a micro-droplet. As shown in panels a, b, and c of FIG. 7, after oocyte 4 is positioned and sperm 10 is added, air can be injected into micro-channel 3 to replace the culture medium, so that micro-droplet 11 is formed in micro-well 7 with oocyte 4 and sperm 10 sealed within. After that, to prevent the evaporation of micro-droplet 11, mineral oil or other fluid in oil phase is injected into micro-channel 3. This method can be used to form a micro-droplet 11 in all micro-wells 7 on micro-well array layer 2 simultaneously. The micro-droplet 11 formed in micro-well 7 is in nanoliter volume. Because of the small volume, it effectively preserves the secretions of the zygote during development, which may improve its development. Additionally, because the fertilization is restricted in a nanoliter volume, the chance of sperm-oocyte interaction dramatically increases. As a result, the number of sperms needed for a successful fertilization is greatly decreased. In addition, the same method can also be implemented to seal the zygote or embryo in a specific stage in the micro-droplet 11 for the embryo culture process.

The embodiments described above are only to exemplify the present invention but not to limit the scope of the present invention, any equivalent modification of variation according to the spirit or technical contents of the present invention is also included within the scope of the present invention.

We claim:

1. A method for single oocyte trapping using an integrated microfluidic device, the method comprising:
   a) providing an integrated microfluidic device for single oocyte trapping, wherein the integrated microfluidic device comprises an upper layer and a lower layer, wherein said lower layer is bound to said upper layer, said upper layer comprises a micro-channel and said lower layer comprises a micro-well array comprising a plurality of micro-wells, said micro-channel is in fluidic connection with said micro-well array, and the height of said micro-channel is greater than the diameter of a mature mammalian oocyte;
   b) transporting an oocyte by a liquid in the micro-channel to allow the oocyte to enter the micro-well array;
   c) adding a sperm to the micro-channel to allow the sperm to reach the oocyte for in vitro fertilization in the micro-well array; and
   d) after the sperm reaches the oocyte, introducing air into the micro-channel to replace the liquid, so that micro-droplets are formed in the micro-wells.

2. The method of claim 1, further comprising adding an oil phase liquid into the micro-channel to seal the micro-droplets, wherein fertilization of the oocyte by the sperm occurs in the sealed micro-droplets.

3. The method of claim 1, wherein the plurality of micro-wells have different depths and/or widths.

4. The method of claim 1, wherein the plurality of micro-wells are of nano-liter volumes.

5. The method of claim 1, wherein the depth of the micro-well array is at least twice the diameter of the mature mammalian oocyte, and the width of the micro-well array is at least 1.5 times the diameter of the mature mammalian oocyte.

6. The method of claim 1, wherein the diameter of the mature mammalian oocyte is about 100 μm.

7. The method of claim 1, wherein the plurality of micro-wells have the same depths and/or widths.

8. The method of claim 1, wherein the depth and/or width of the micro-well array is greater than the diameter of the mature mammalian oocyte.

9. The method of claim 1, wherein the depth and/or width of the micro-well array is at least twice the diameter of the mature mammalian oocyte.

10. The method of claim 1, wherein the micro-channel defines a direction of the fluidic flow in the micro-channel, and wherein the plurality of micro-wells are distributed in parallel and/or perpendicular to the direction of the fluidic flow in the micro-channel.

11. The method of claim 1, wherein the micro-well array covers the width of the micro-channel.

12. The method of claim 1, wherein a distance between adjacent micro-well rows is less than ¼, ⅓, or ½ of the width of the micro-wells.

13. The method of claim 1, wherein the shape of the micro-wells have a shape in the form of a square or a circle.

14. The method of claim 1, wherein the micro-wells have the same or different shapes.

15. The method of claim 1, wherein the upper layer and/or lower layer is made of a transparent material.

16. The method of claim 1, wherein a layer of reflective material is attached beneath the micro-well array.

17. The method of claim 1, wherein the upper layer is reversibly bound to the lower layer.

18. The method of claim 1, wherein the upper layer further comprises an inlet and/or an outlet to the micro-channel.

19. A method for single oocyte trapping using an integrated microfluidic device the method comprising:
   a) providing an integrated microfluidic device for single oocyte trapping, wherein the integrated microfluidic device comprises an upper layer and a lower layer, wherein said lower layer is bound to said upper layer, said upper layer comprises a micro-channel and said lower layer comprises a micro-well array comprising a plurality of micro-wells, said micro-channel is in fluidic connection with said micro-well array, and the height of said micro-channel is greater than the diameter of a mature mammalian oocyte;
   b) transporting an oocyte by a first liquid in the micro-channel to allow the oocyte to enter the micro-well array;
   c) adding sperm to the micro-channel to allow the sperm to reach the oocyte for in vitro fertilization in the micro-well array;
   d) adding a second liquid to the micro-channel, wherein dead sperm(s) and cell debris in said micro-channel are removed to facilitate further development of the fertilized oocyte or development of an embryo from the fertilized oocyte; and
   e) after fertilization of the oocyte or development of the fertilized oocytes or the embryo, introducing air into the micro-channel to replace the second liquid, so that micro-droplets are formed in the micro-wells.

20. The method of claim 19, further comprising adding an oil phase liquid into the micro-channel to seal the micro-droplets, wherein development of the fertilized oocyte or the embryo occurs in the sealed micro-droplets.

21. The method of claim 19, wherein the plurality of micro-wells have different depths and/or widths.

22. The method of claim 19, wherein the plurality of micro-wells are of nano-liter volumes.

23. The method of claim 19, wherein the depth of the micro-well array is at least twice the diameter of the mature mammalian oocyte, and the width of the micro-well array is at least 1.5 times the diameter of the mature mammalian oocyte.

24. The method of claim 19, wherein the diameter of the mature mammalian oocyte is about 100 μm.

25. The method of claim 19, wherein the plurality of micro-wells have the same depths and/or widths.

26. The method of claim 19, wherein the depth and/or width of the micro-well array is greater than the diameter of the mature mammalian oocyte.

27. The method of claim 19, wherein the depth and/or width of the micro-well array is at least twice the diameter of the mature mammalian oocyte.

28. The method of claim 19, wherein the micro-channel defines a direction of the fluidic flow in the micro-channel, and wherein the plurality of micro-wells are distributed in parallel and/or perpendicular to the direction of the fluidic flow in the micro-channel.

29. The method of claim 19, wherein the micro-well array covers the width of the micro-channel.

30. The method of claim 19, wherein a distance between adjacent micro-well rows is less than ¼, ⅓, or ½ of the width of the micro-wells.

31. The method of claim 19, wherein the shape of the micro-wells have a shape in the form of a square or a circle.

32. The method of claim 19, wherein the micro-wells have the same or different shapes.

33. The method of claim 19, wherein the upper layer and/or lower layer is made of a transparent material.

34. The method of claim 19, wherein a layer of reflective material is attached beneath the micro-well array.

35. The method of claim 19, wherein the upper layer is reversibly bound to the lower layer.

36. The method of claim 19, wherein the upper layer further comprises an inlet and/or an outlet to the micro-channel.

37. The method of claim 19, further comprising retrieving the fertilized oocyte or the embryo from the micro-well array.

38. The method of claim 37, wherein the upper layer is removed from the lower layer to expose the micro-well array for retrieving the fertilized oocyte or the embryo from the micro-well array.

39. The method of claim 19, wherein one end of the micro-channel is connected with a syringe pump, and wherein the second liquid is injected by positive or negative pressure.

40. The method of claim 19, wherein the second liquid stays still, or flows constantly, during the development of the fertilized oocyte or the embryo.

41. The method of claim 19, wherein the second liquid flows intermittently during the development of the fertilized oocyte or the embryo.

* * * * *

UNITED STATES PATENT AND TRADEMARK OFFICE
CERTIFICATE OF CORRECTION

PATENT NO. : 9,445,840 B2  
APPLICATION NO. : 13/805322  
DATED : September 20, 2016  
INVENTOR(S) : Chao Han et al.

Page 1 of 1

It is certified that error appears in the above-identified patent and that said Letters Patent is hereby corrected as shown below:

On the Title Page

Item (73) Assignees should read: CapitalBio Corporation, Beijing (CN); Tsinghua University, Beijing (CN)

Signed and Sealed this
Eleventh Day of April, 2017

Michelle K. Lee
*Director of the United States Patent and Trademark Office*